United States Patent [19]
McCulloch

[11] Patent Number: 5,340,404
[45] Date of Patent: Aug. 23, 1994

[54] PROCESS FOR SEPARATING ALLOSE FROM OTHER SUGARS

[75] Inventor: Beth McCulloch, Clarendon Hills, Ill.

[73] Assignee: UOP, Des Plaines, Ill.

[21] Appl. No.: 60,074

[22] Filed: May 12, 1993

[51] Int. Cl.$^5$ .............. C13J 1/06; B01D 15/08; B01D 15/04; C07H 3/02

[52] U.S. Cl. .............. 127/46.2; 536/124; 536/127; 210/690; 210/667; 210/659; 210/656; 210/635

[58] Field of Search .............. 127/46.2; 536/124, 127; 210/690, 667, 635, 656, 659

[56] References Cited

U.S. PATENT DOCUMENTS

| | | | |
|---|---|---|---|
| 4,226,977 | 10/1980 | Neuzil et al. | 536/1 |
| 4,319,929 | 3/1982 | Fickel | 127/46.2 |
| 4,340,724 | 7/1982 | Neuzil et al. | 127/46.2 |
| 4,358,322 | 11/1982 | Neuzil et al. | 127/46.2 |
| 4,442,285 | 4/1984 | Neuzil et al. | 127/46.2 |
| 4,519,845 | 5/1985 | Ou | 127/46.2 |
| 4,581,447 | 4/1986 | Arena | 536/125 |
| 4,837,315 | 6/1989 | Kulprathipanja | 536/127 |
| 4,880,919 | 11/1989 | Kulprathipanja | 536/127 |
| 4,963,382 | 10/1990 | Arena et al. | 426/548 |
| 5,000,794 | 3/1991 | Kulprathipanja | 210/690 |

FOREIGN PATENT DOCUMENTS 1540556  2/1979  United Kingdom ........ C13K 13/00

Primary Examiner—Paul Lieberman
Assistant Examiner—Patricia L. Hailey
Attorney, Agent, or Firm—Thomas K. McBride; John F. Spears, Jr.

[57] ABSTRACT

D-Allose, a sweet non caloric sugar, is recovered from an aqueous solution containing at least on other monosaccharide by adsorptive separation using a calcium loaded ion exchange resin as the adsorbent.

6 Claims, No Drawings

PROCESS FOR SEPARATING ALLOSE FROM OTHER SUGARS

BACKGROUND OF THE INVENTION

1. Field of the Invention

This invention relates to the separation of allose, a rare sugar, from aqueous solutions resulting from allose preparation steps, with these solutions containing a diverse mixture of sugars and possibly other carbohydrates. The invention also relates to the separation by selective adsorption of allose by certain cation exchange resins.

2. Background of the Invention

Artificial sweeteners are receiving increased attention as low caloric content dietary aids. One specific class or type of artificial sweetener is the L sugars. These sugars tend to have desirable sweetness but are not believed to be metabolized in the human body and therefore do not provide caloric intake. While therefore appearing to be excellent low-calorie sweeteners, many L-sugars are plagued by undesired physiological effects which make them unsuitable for most food products.

Efforts are still being made to locate natural sugars having the desired qualities of sweetness, low caloric value and no adverse physiological effects. One focus of these efforts is investigation of rare sugars, such as allose, which must be produced from other sugars and then recovered by some series of separation steps such as crystallization or adsorption.

RELATED ART

U.S. Pat. No. 4,963,382 issued to B.J. Arena and E.C. Arnold describes the utility of d-allose as a reduced calorie sugar which tastes sweet, provides bulk and undergoes a browning reaction upon baking. The d-allose of this reference was made commercially accessible by the technology of U.S. Pat. No. 4,581,447 also issued to Arena.

The use of cross-linked ion exchange resins to perform specific sugar separations is also known in the art. For instance, U.S. Patent 4,519,845 issued to D Ou describes the separation of sucrose from molasses using an adsorbent comprising an admixture of an ion retardation resin and a calcium and potassium cation exchanged sulfonated styrene cation exchange resin. U.S. Pat. No. 4,837,315 issued to S. Kulprathipanja describes the separation of mannose from mixtures of glucose and other saccharides representative of that resulting from the epimerization of L-glucose using a calcium/ammonium exchanged polystyrene divinylbenzene cross-linked ion exchange resin.

The adsorptive separation of mannose from an aqueous mixture of glucose and mannose through the use of a calcium exchanged cation exchange resin is described in British Patent Specification 1,540,556.

Resins are widely used as adsorbents in commercial adsorptive separation processes. This has resulted in a substantial body of art directed to the use of resins as represented by U.S. Pat. No. 4,319,929 issued to R.G. Fickel.

BRIEF SUMMARY OF THE INVENTION

The invention is an adsorptive process for separating allose from admixture with other monosaccharides. The adsorbent is a calcium exchanged cross-linked divinyl benzene resin. Water is utilized as the desorbent.

One embodiment of the invention may be characterized as a process for separating allose from an aqueous mixture comprising allose and at least one other monosaccharide, which process comprises contacting said mixture at adsorption conditions with an adsorbent comprising a calcium exchanged ion exchange resin, selectively adsorbing said allose, removing the nonadsorbed portion of said mixture from contact with said adsorbent and recovering allose by desorption with a desorbent comprising water at desorption conditions.

DETAILED DESCRIPTION OF THE INVENTION AND PREFERRED EMBODIMENTS

As described in the previously cited U.S. Pat. No. 4,963,382 to B.J. Arena D-allose has desirable properties as a low calorie sweetener. This patent is incorporated herein by reference for its teaching as to the utility and use of allose for this purpose. It is an objective of the invention to provide an improved process for separating allose from aqueous mixtures containing allose and at least one other monosaccharide such as mannose and glucose.

This objective of the subject invention is achieved through the use of an adsorbent comprising a calcium exchanged ion exchange resin. A styrene divinyl benzene resin is preferred. Suitable resins are available for purchase from known resin suppliers. Suggested resins for this separation are Dowex 99 from Dow Chemical Company of Midland Mich., ADS-250 sold by UOP of Des Plaines, Ill. and HPX87C sold by Biorad Incorporated. It is preferred that the resin is highly exchanged with calcium ions. It is therefore preferred that at least 95% and preferably over 98% of the ion exchange capacity of the resin has been effected by replacement with calcium ions.

In the process of the present invention D-allose is separated from an aqueous feed mixture containing other saccharides. This feed mixture is expected to be formed by the epimerization of glucose. The process is effected by passing a feed mixture over an adsorbent which selectively adsorbs the d-allose while permitting other components of the feed stream to pass through the adsorption zone in an unchanged condition. The flow of the feed is through this specific zone is then stopped and the adsorption zone is flushed to remove nonadsorbed materials surrounding the adsorbent. Thereafter the allose is desorbed from the adsorbent by treating the adsorbent with a desorbent material, preferably water. The desorbent material is commonly also used to flush the nonadsorbed materials from the adsorbent.

For purposes of this invention, the various terms used herein are intended to have meanings consistent with the following definitions. A "feed mixture" is a mixture containing one or more extract components and one or more raffinate components to be separated by the process. The term "feed stream" indicates a stream of a feed mixture which passes to the adsorbent used in the process. An "extract component" is a compound or class of compound that is more selectively adsorbed by the adsorbent while a "raffinate component" is a compound or type of compound that is less selectively adsorbed. The term "desorbent material" shall mean generally a material capable of desorbing an extract component. The term "raffinate stream" or "raffinate output stream" means a stream in which a raffinate component is removed from the adsorbent bed. The composition of the raffinate stream can vary from essentially 100% desorbent material to essentially 100% raffinate components. The term "extract stream" or "extract output stream" shall mean a stream in which an extract material which has been desorbed by a desorbent material is removed from the adsorbent bed. The composition of the extract stream, likewise, can vary from essentially 100% desorbent material to essentially 100% extract components. At least a portion of the extract stream and preferably, at least a portion of the raffinate stream from the separation process are passed to separation means, typically fractionators, where at least a portion of desorbent material is recovered to produce an extract product and a raffinate product. The terms "extract product" and "raffinate product" mean products produced by the process containing, respectively, an extract component and a raffinate component in higher concentrations than those found in the extract stream and the raffinate stream.

In carbohydrate adsorptive separation processes, which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component or both would complicate or prevent product recovery.

Since both the raffinate stream and the extract stream typically contain desorbent materials, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. It is contemplated that at least a portion of the desorbent material will be separated from the extract and the raffinate streams by distillation or evaporation, but other separation methods such as reverse osmosis may also be employed alone or in combination with distillation or evaporation. Since the raffinate and extract products herein are foodstuffs intended for human consumption, desorbent materials should also be nontoxic. Finally, desorbent materials should also be materials which are readily available and, therefore, reasonable in cost.

A dynamic testing "pulse test" apparatus may be employed to test various adsorbents with a particular feed mixture and desorbent material to measure the adsorbent characteristics of adsorptive capacity, selectivity, resolution and exchange rate. The apparatus consists of a tubular adsorbent chamber of for instance 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to an outlet line of the chamber and used to detect or measure the concentration of one or more components in the effluent stream leaving the adsorbent chamber. A pulse test, performed using this apparatus and the following general procedure, may be used to determine selectivities, resolution and other data for various adsorbent-desorbent systems.

In a pulse test the adsorbent is filled to equilibrium with a particular desorbent material by passing the desorbent material through the adsorbent chamber. The feed mixture, diluted in desorbent if desired, is injected for a duration of several minutes. Desorbent flow is resumed, and the feed components are eluted as in a liquid-solid chromatographic operation. The effluent can be analyzed on-stream or, alternatively, effluent samples can be collected periodically and later analyzed separately and traces of the envelopes of corresponding component peaks developed.

From information derived from the test, adsorbent performance can be rated in terms of void volume, retention volume for an extract or a raffinate component, selectivity for one component with respect to the other, the resolution between the components and the rate of desorption of an extract component by the desorbent. The retention volume of an extract or a raffinate component may be characterized by the distance between the center of the peak envelope of an extract or a raffinate component and the peak envelope of a tracer component or some other known reference point. It is expressed in terms of the volume in cubic centimeters of desorbent pumped during this time interval represented by the distance between the peak envelopes.

Retention volumes for good candidate systems fall within a range set by extrapolation to commercial designs. A very small retention volume indicates there is little separation between the two components. (One component is not adsorbed strongly enough.) Large extract retention volumes indicate it is difficult for the desorbent to remove the retained extract compound. In terms of the pulse test described herein retention volumes in the broad range of about 30–50 cc's are desired.

In a commercial unit the adsorbent may be employed in the form of a dense compact fixed bed which is alternately contacted with the feed mixture and desorbent materials. In the simplest embodiment of the invention, the adsorbent is employed in the form of a single static bed in which case the process is only semicontinuous. In another embodiment, a set of two or more static beds may be employed with appropriate valving so that the feed mixture is passed through one or more adsorbent beds while the desorbent materials can be passed through one or more of the other beds in the set. The flow of feed mixture and desorbent materials may be either upward or downward through the desorbent.

Any of the conventional apparatus employed in static bed fluid-solid contacting may be used. Countercurrent moving bed or simulated moving bed countercurrent flow systems, however, have a much greater separation efficiency than simpler fixed bed adsorbent systems and are, therefore, preferred for commercial installations. In the moving bed or simulated moving bed processes, the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589, incorporated by reference herein. In such a system, it is the progressive movement of multiple liquid access points down an adsorbent chamber that simulates the upward movement of adsorbent contained in the chamber. Only four of the access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller is provided to set and regulate these flow rates.

The active liquid access points effectively divide the adsorbent chamber into separate zones, each of which has a different function. In this embodiment of the present process, it is generally necessary that three separate operational zones be present in order for the process to take place, although, in some instances, an optional fourth zone may be used. The zone numbers used in this description of a simulated moving bed process are those used in U.S. Pat. Nos. 3,392,113 and 4,475,954 which are also incorporated herein by reference for their teaching on the use of simulated moving bed technology.

Although both liquid and vapor phase operations can be used in many adsorptive separation processes, liquid-phase operation is preferred for this process because of the nature of the materials being separated. Adsorption conditions will include a temperature range of from about 20° to about 200° C., with 20° to about 100° C. being preferred and a pressure range of from about atmospheric to about 500 psig as required to insure liquid phase with from about atmospheric to about 250 psig being preferred. Increased temperature tends to reduce retention volumes. Desorption conditions will preferably include the same range of temperatures and pressures as used for adsorption conditions.

The size of the units which can utilize the process of this invention can vary anywhere from those of pilot plant scale (see, for example, U.S. Pat. No. 3,706,812 assigned to UOP) to those of commercial scale and can range in flow rates from as little as a few cc's an hour up to many thousands of gallons per hour.

Another embodiment of a simulated moving bed flow system suitable for use in the process of the present invention is the cocurrent high efficiency simulated moving bed process disclosed in U.S. Pat. Nos. 4,402,832 and 4,478,721 to Gerhold, incorporated by reference herein in its entirety. This process may be preferred, because of its energy efficiency and lower capital costs, where products of slightly lower purity are acceptable.

The examples shown below are intended to further illustrate the process of this invention and are not intended to be construed as unduly limiting the scope and spirit of the claimed process.

EXAMPLE 1

The subject process was performed using a pulse test apparatus as described above. The test was performed at a temperature of 65° C. and a superficial velocity in the adsorbent bed of 1.47 cc/minute in a column having an adsorbent capacity 126.00 cc. The adsorbent was a Dowex 99 resin ion exchanged to contain 9 wt. % calcium. The desorbent was deionized water. The tests were performed with a feed pulse of 5 cc, with the feed pulse containing 10 wt. % calcium chloride (used as tracer), glucose, mannose and 5% allose. The test results indicated a net retention volume of 9.9 for glucose, 16.5 for mannose and 33.1 for allose indicating this system could be employed for commercial scale separation and recovery of allose. Pulse test data is sometimes reported in terms of a selectivity $\beta$. $\beta$ is defined as the ratio of the net retention volume of the more strongly adsorbed component to each of the other components and is described in more detail in U.S. Pat. No. 5,000,794. The selectivity values for glucose and mannose were 3.3 and 2.0 respectively versus allose as the reference.

EXAMPLE 2

The subject process was performed a second time using the pulse test apparatus. This test was performed at a temperature of 85° C. and a superficial velocity in the adsorbent bed of 0.4 cc/minute. The adsorbent was a Biorad HPLC column containing HPX-87C resin ion exchanged to contain 9% calcium. The desorbent was deionized water. The tests were performed by injecting calcium chloride, glucose, mannose, allose and altrose solutions to the column. The test results indicated a net retention time of 5.31 minutes for glucose, 8.03 for mannose, 8.31 for altrose and 14.13 for allose indicating this system could also be employed for commercial scale separation and recovery of allose. These retention volumes result in selectivities, $\beta$, of 1.0 for allose, 1.7 for altrose, 1.8 for mannose and 2.7 for glucose.

The strength of the desorbent is an important factor in the success of a selective adsorption process. For instance a stronger desorbent may allow the use of a more selective adsorbent having an otherwise unacceptably high product retention volume. The preferred desorbent for the subject process comprises water. However, it is contemplated that other compounds such as alcohols could be present in the desorbent in addition to water in order to optimize the desorbent's capabilities. Ethanol is the preferred alcohol since a small amount of residual ethanol should be more acceptable in the recovered product than the other low cost light alcohols. Other monohydric alcohols could be used if acceptable in the product or they can be removed to acceptable levels.

One embodiment of the invention may accordingly be characterized as a continuous process for separating D-allose from an aqueous mixture comprising d-allose, mannose, glucose and altrose, which process comprises contacting said mixture with an adsorbent comprising a calcium exchanged cross-linked ion exchange resin, selectively adsorbing said allose, removing the nonadsorbed portion of said mixture from contact with said adsorbent and recovering said allose by desorption with a desorbent comprising water at desorption conditions.

What is claimed is:

1. A process for separating allose from an aqueous mixture comprising allose and at least one other monosaccharide, which process comprises contacting said mixture at adsorption conditions with an adsorbent comprising an ion exchange resin, selectively adsorbing said allose, removing the nonadsorbed portion of said mixture from contact with said adsorbent and recovering allose by desorption with a desorbent comprising water at desorption conditions.

2. The process of claim 1 wherein said adsorption and desorption conditions include a temperature range of from about 20° to about 100° C. and a pressure range of from about atmospheric to about 250 psig.

3. The process of claim 1 wherein said adsorbent is a calcium exchanged resin.

4. A process for separating D-allose from an aqueous mixture comprising D-allose and altrose, which process comprises contacting said mixture with an adsorbent comprising a calcium exchanged cross-linked ion exchange resin, selectively adsorbing said allose, removing the nonadsorbed portion of said mixture from contact with said adsorbent and recovering said allose by desorption with a desorbent comprising water at desorption conditions.

5. The process of claim 4 wherein said admixture also contains glucose.

6. The process of claim 5 wherein said admixture also comprises mannose.

* * * * *